United States Patent
Hou et al.

(10) Patent No.: US 11,491,135 B2
(45) Date of Patent: Nov. 8, 2022

(54) MEDICAL USE OF TECTORIGENIN IN TREATMENT OF CHICKEN NECROTIC ENTERITIS

(71) Applicants: SHANDONG GUANGYUAN PHARMACEUTICAL SCI. & TECH.CO., LTD, Shandong (CN); SHANDONG JINZHUJI PHARMACEUTICAL CO., LTD, Shandong (CN)

(72) Inventors: Yunfeng Hou, Shandong (CN); Xuming Deng, Jilin (CN); Chuanjin Zhang, Shandong (CN); Shui Liu, Jilin (CN); Jianfeng Wang, Jilin (CN); Youzhi Li, Shandong (CN); Jing Nie, Shandong (CN); Junping Zhu, Shandong (CN); Guizhen Wang, Shandong (CN); Yong Zhang, Shandong (CN); Xiaoye Fan, Shandong (CN); Jian Zhang, Jilin (CN); Tingting Wang, Jilin (CN); Yonglin Zhou, Jilin (CN); Qianghua Lv, Shandong (CN)

(73) Assignees: SHANDONG GUANGYUAN PHARMACEUTICAL SCI. & TECH.CO., LTD, Shandong (CN); SHANDONG JINZHUJI PHARMACEUTICAL CO., LTD, Shandong (CN)

( * ) Notice: Subject to any disclaimer, the term of this patent is extended or adjusted under 35 U.S.C. 154(b) by 179 days.

(21) Appl. No.: 16/963,208

(22) PCT Filed: May 14, 2019

(86) PCT No.: PCT/CN2019/086738
§ 371 (c)(1),
(2) Date: Jul. 17, 2020

(87) PCT Pub. No.: WO2019/218986
PCT Pub. Date: Nov. 21, 2019

(65) Prior Publication Data
US 2021/0121439 A1    Apr. 29, 2021

(51) Int. Cl.
*A61K 31/353* (2006.01)
*A61P 31/04* (2006.01)
*A61P 1/00* (2006.01)

(52) U.S. Cl.
CPC .............. *A61K 31/353* (2013.01); *A61P 1/00* (2018.01); *A61P 31/04* (2018.01)

(58) Field of Classification Search
None
See application file for complete search history.

(56) References Cited

FOREIGN PATENT DOCUMENTS

| CN | 101011378 A | 8/2007 |
|----|-------------|--------|
| CN | 101185707 A | 5/2008 |
| CN | 108309969 A | 7/2018 |

OTHER PUBLICATIONS

International Search Report for PCT/CN2019/086738 dated Aug. 12, 2019, ISA/CN.
Yang, Enci et al. "Research Progress on Pharmacological Effects of Tectorigenin", Central South Pharmacy, vol. 9, No. 12, Dec. 31, 2011, pp. 913-916.

*Primary Examiner* — Samantha L Shterengarts
(74) *Attorney, Agent, or Firm* — Yue (Robert) Xu; Apex Attorneys at Law, LLP

(57) ABSTRACT

Provided is use of tectorigenin in the preparation of a medicament for treatment of chicken necrotic enteritis. Using tectorigenin for treating chicken necrotic enteritis can significantly reduce the degree of pathological changes in the intestinal tract of chickens with necrotic enteritis, and has a good therapeutic effect on chicken necrotic enteritis caused by *Clostridium perfringens*.

3 Claims, 3 Drawing Sheets

MEDICAL USE OF TECTORIGENIN IN TREATMENT OF CHICKEN NECROTIC ENTERITIS

CROSS REFERENCE TO RELATED APPLICATIONS

Figure 1:
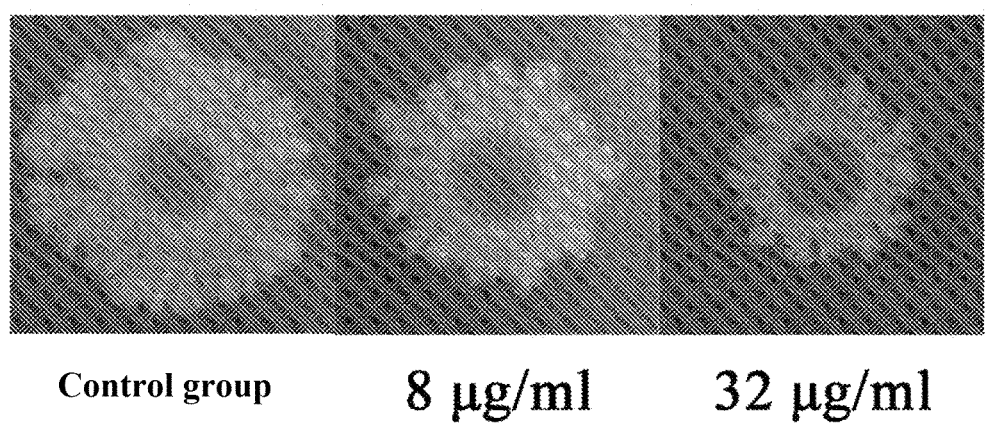

This application is the national phase of International Application No. PCT/CN2019/086738, titled "MEDICAL USE OF TECTORIGENIN IN THE TREATMENT OF CHICKEN NECROTIC ENTERITIS", filed on May 14, 2019, which claims the priority of Chinese Patent Application No. 201810470739.7, filed on May 17, 2018, filed with China National Intellectual Property Administration, and titled with "MEDICAL USE OF TECTORIGENIN IN THE TREATMENT OF CHICKEN NECROTIC ENTERITIS", and the disclosures of which are hereby incorporated by reference.

FIELD

The present disclosure discloses the medical use of tectorigenin in the treatment of chicken necrotic enteritis, and relates to the application of tectorigenin in the preparation of a medicament for the treatment of chicken necrotic enteritis, which belongs to the field of medicament technology.

BACKGROUND

*Clostridium perfringens* is an anaerobic Gram-positive bacillus and widely present in soil, water, food, human and animal feces, livestock feed and intestinal tract of animals in nature. *Clostridium perfringens* is a normal intestinal flora of human and animals and belongs to conditional pathogen. Currently, *Clostridium perfringens* are divided into five serotypes A-E according to different exotoxins they secreted. Poultry are mainly infected with *Clostridium perfringens* type A and C, especially type A. After infecting poultry, *Clostridium perfringens* mainly cause necrotic enteritis, the symptoms of which are depression, fluffy and untidy plume, reduced or no appetite, bloody stool and severely reduced production performance for chickens. Lesions are mainly in small intestine, which is characterized by thinning of intestinal wall, and focal or piece of necrosis and shedding of intestinal mucosa. According to relevant research statistics, the economic loss caused by necrotic enteritis in global poultry industry has reached billions of dollars, which has seriously endangered the development of poultry industry.

The adhesion colonization of *Clostridium perfringens* in intestinal tract is mainly mediated by its Type IV pili (TFP). TFP is a kind of movement organ that exists on cell membrane of bacteria. TFP endows *Clostridium perfringens* an ability of moving in its natural habitat and on the surface of semi-solid media such as soft and hard agar and the like. This special movement is referred as Gliding motility. According to research, bacterial functions, including adhesion colonization, gliding motility and biofilm formation and the like of *Clostridium perfringens* in intestinal tract, are all somewhat related to TFP. By inhibiting functions of TFP of *Clostridium perfringens*, it's possible to interfere with adhesion colonization of bacteria in intestinal tract, so as to achieve the purpose of resisting *Clostridium perfringens* infection.

Adding antibiotics to feed is a main approach for the prevention and treatment of poultry infected with necrotic enteritis. However, problems of bacterial resistance and antibiotic residue caused by the large-scale use of antibiotics poses a serious threat to public health. Therefore, development of safe and effective antibiotic alternatives is increasingly becoming a hotspot in research. Natural compounds have advantages such as low toxicity, abundant sources, and wide range of safety and the like, and are important resources for screening antibiotic alternatives.

Tectorigenin is a naturally-occurring isoflavonoid compound and mainly present in roots and stems of *Iridaceae iris l.* and *Belamcanda adans* plants. Current researches have showed that tectorigenin has biological activities such as anti-inflammatory, anti-cancer, hepatoprotective, antioxidant and estrogen-like effects, and the like. In recent years, a large amount of literature has reported pharmacological activities of tectorigenin. However, up to now, there is no relevant research on using tectorigenin for the treatment of chicken necrotic enteritis caused by *Clostridium perfringens* around the world.

SUMMARY

The present disclosure provides medical use of tectorigenin in the treatment of chicken necrotic enteritis, and tectorigenin has a good therapeutic effect on chicken necrotic enteritis caused by *Clostridium perfringens*.

The molecular structure of the tectorigenin in the present disclosure is as follows:

Molecular formula: $C_{16}H_{12}O_6$;
molecular weight: 300.263

The present disclosure verifies that tectorigenin has a protective effect on chicken necrotic enteritis caused by *Clostridium perfringens* infection through inhibition test of gliding motility of *Clostridium perfringens*, inhibition test of biofilm formation, and chicken necrotic enteritis model test.

I. Inhibition Test of Gliding Motility

The standard strain of *Clostridium perfringens* ATCC13124 was cultured anaerobically in liquid BHI medium at 37° C. for 12 h, and then 300 µl of the culture was taken and continued to be cultured anaerobically in liquid BHI at 37° C. for 5 h. 1 ml of the culture was taken and centrifuged at 10,000 g to discard supernatant. The bacterium obtained were resuspended in 500 µl of BHI liquid medium to double the concentration. Subsequently, 5 µl of the concentrated bacterial solution was taken and added dropwise respectively to 0.7% BHIA plates containing 8 µg/ml and 32 µg/ml tectorigenin, which were prepared previously and dried in an oven at 37° C. for 1 h. The plates were cultured anaerobically at 37° C. for 48 h, and images were collected (see FIG. 1). The result showed that 8 µg/ml and 32 µg/ml tectorigenin can both significantly inhibit the gliding motility of *Clostridium perfringens* on BHIA, and the effect of 32 µg/ml tectorigenin was more remarkable.

II. Inhibition Test of Biofilm Formation

Figure 2:
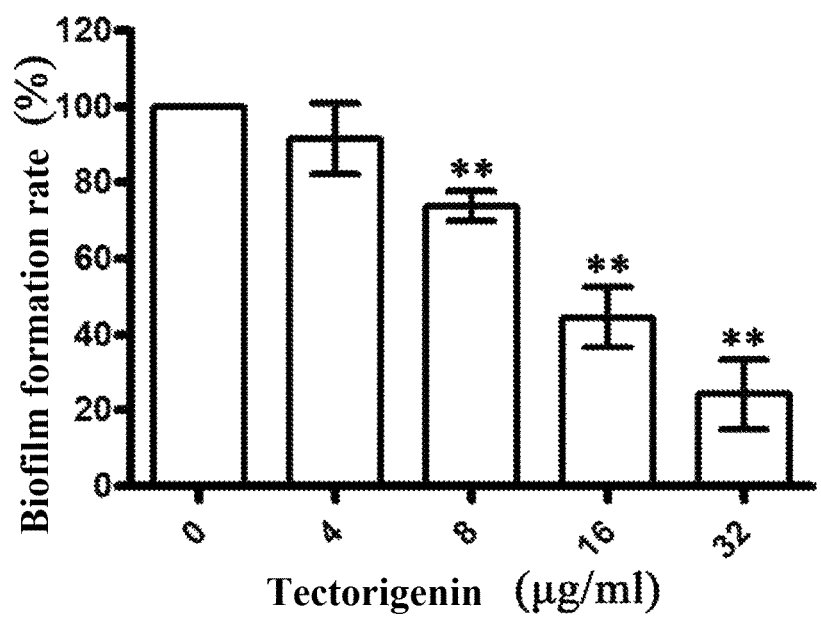
Figure 3:
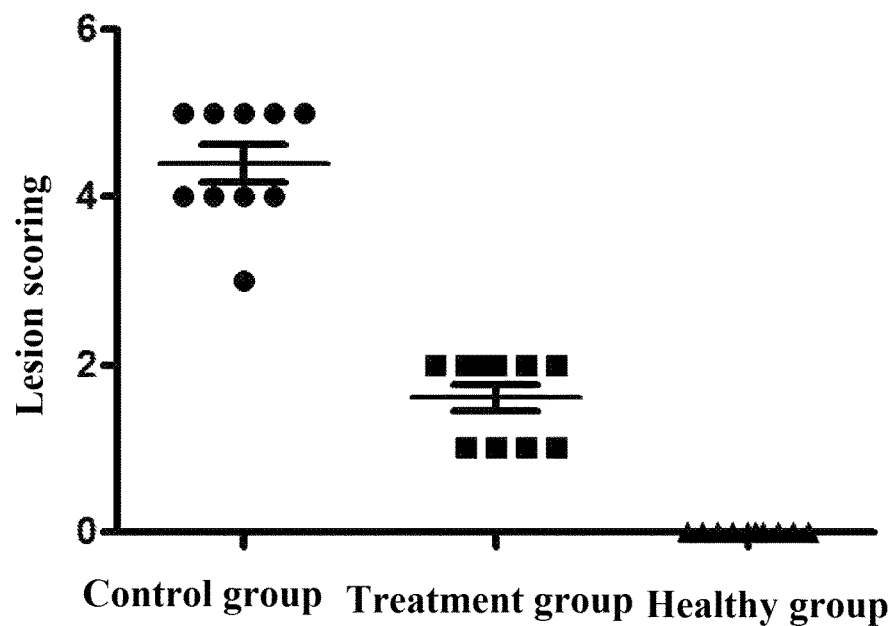
Figure 4:
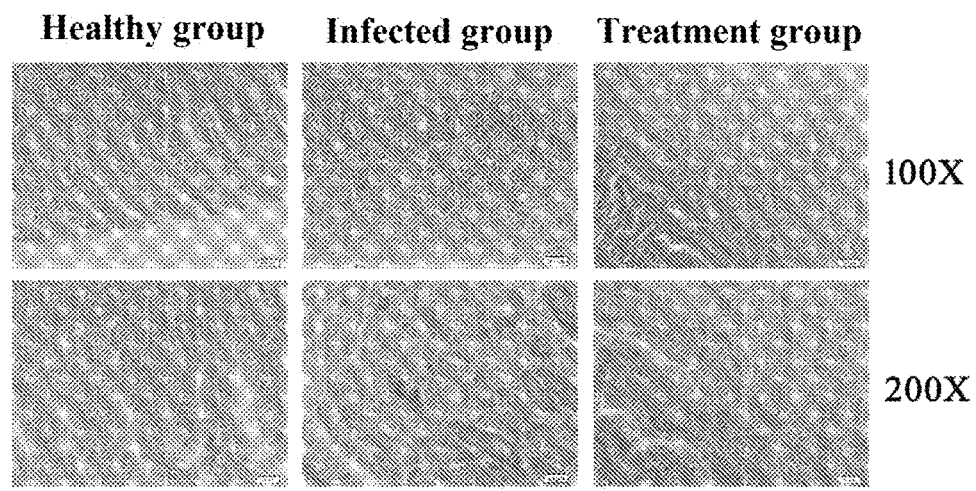
Figure 5:
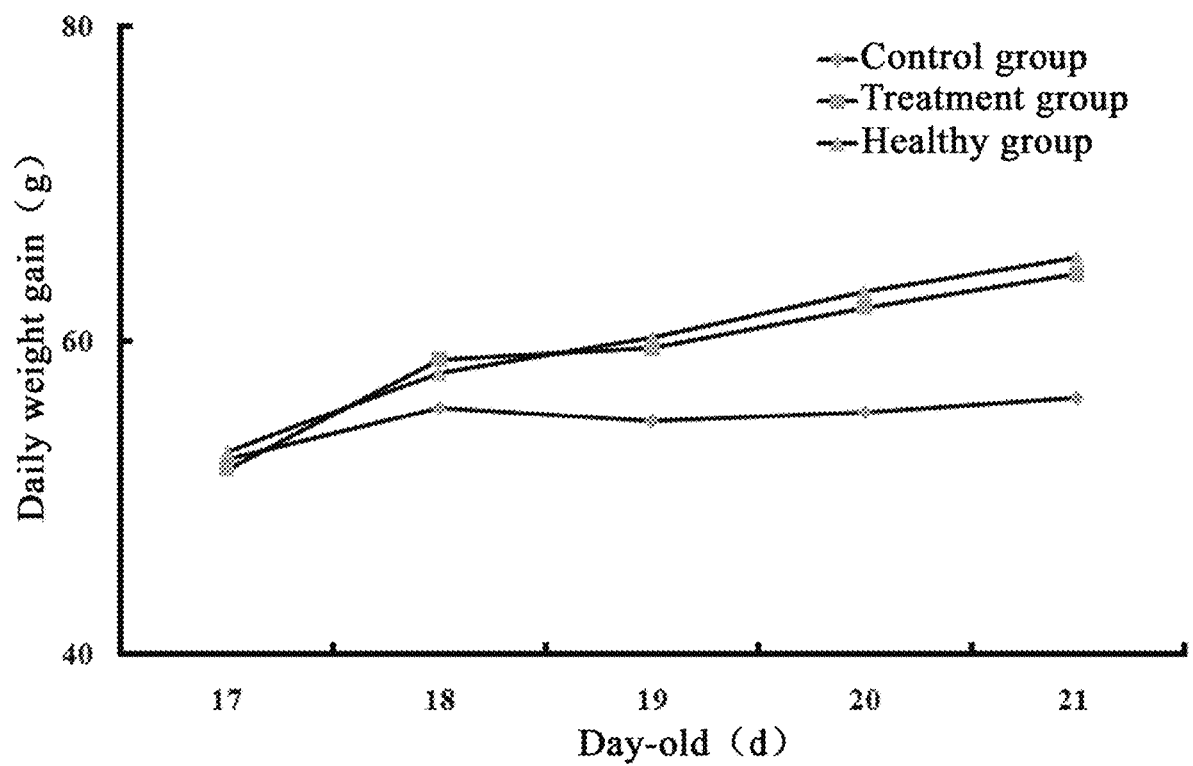

*Clostridium perfringens* were cultured anaerobically in liquid BHI at 37° C. for 12 h, and then centrifugation was conducted to discard supernatant. The bacterium obtained were washed once with sterile PBS, and then resuspended in TSB liquid medium and adjusted to $OD_{600\ nm}$=0.1. 400 μl of adjusted bacteria culture was taken and added to 24-well plate. Subsequently, different concentrations of tectorigenin were respectively added to the bacterial culture, such that the final concentration of tectorigenin in 24-well plate was 4 μg/ml, 8 μg/ml, 16 μg/ml and 32 μg/ml respectively. Additionally, a positive control group with addition of 0.4 μl filter-sterilized DMSO (without addition of tectorigenin) and a negative control group of 400 μl liquid TSB medium were prepared, and added respectively to 24-well plate to anaerobically culture at 30° C. for 5 days. The supernatant was then discarded by aspiration. The plate was washed twice with sterilized PBS, and dried at room temperature for 30 min. The plate was added with 400 μl of filter-sterilized 1% crystal violet, and incubated at room temperature for 30 min. Crystal violet was then discarded. The plate was washed twice with sterilized PBS again. 33% acetic acid was added in each well to dissolve the crystal violet. After pipetting and mixing homogeneously, 300 μl of the solution was taken and added to 3 separate wells with 100 μl per well of 96-well plate respectively. The absorbance was measured at 570 nm using a microplate reader, and the biofilm formation rate was calculated based on the absorbance of crystal violet. The result showed that tectorigenin can effectively inhibit the biofilm formation of *Clostridium perfringens* (see FIG. 2).

III. Therapeutic Study of Chicken Necrotic Enteritis Model Test

1. Chicken Necrotic Enteritis Model 17-day-old male Arbor Acre broiler chickens were orally administered 0.5 ml ($1\times10^9$ CFUs) of *Clostridium perfringens* ATCC13124 culture resuspended in sterile PBS. On the next day (18-day-old), the bacteria solution having the same bacteria amount was administered again to challenge bacteria, so as to establish a model of chicken necrotic enteritis. The chickens in the healthy group were orally administered 0.5 ml of sterile PBS as a control.

2. Intestinal Lesion Score Test

Chickens were orally administered with 25 mg/kg of tectorigenin (dissolved in sterilized PBS) once every 12 h according to body weight of chickens 4 h before oral bacteria challenge infection (17-day-old). In addition, a positive control group without medicament treatment and a healthy control group without bacteria challenge infection were prepared. The chickens in the positive control group and healthy control group were weighed in the same way and were orally administered corresponding volume of sterile PBS according to body weight. Each of the above three groups has 10 chickens, and the treatment group has a total of 5 days of treatment with medicament administration (treatment to 21-day-old). All chickens were sacrificed at 21-day-old by cervical dislocation. Autopsy was performed and the duodenum to the jejunum was taken out. The pathological changes in the intestinal tract were observed visually, and intestinal injury scoring was performed according to the degree of intestinal injury (see FIG. 3). The intestinal injury scoring was based on a 0-6 scores system: 0 score (with no obvious injury), 1 score (the bowel wall becoming thin and brittle), 2 scores (with 1-5 necrotic lesions), 3 scores (with 6-15 necrotic lesions), 4 scores (with 16 or more necrotic lesions), 5 scores (with a 2-3 cm piece in length of necrosis), 6 scores (with a large area of diffuse necrosis). In addition, diseased materials was collected in the above-mentioned small intestine, and was subjected to HE staining to make pathological sections. The histopathological changes were observed under a microscope (see FIG. 4).

During the bacteria challenge, all broiler chickens were weighed daily, and the average body weight and daily weight gain were calculated to investigate the effect of tectorigenin on the daily weight gain of broiler chickens with necrotic enteritis after treating with tectorigenin (see FIG. 5).

The result of intestinal lesions scoring showed that after the treatment with tectorigenin, the degree of pathological changes of the necrotic enteritis in the intestinal tract of chickens was significantly reduced. Histopathological observations showed that the intestinal villus of small intestine for broiler chickens in the healthy group were intact in structure, without bleeding and inflammatory exudation; while the intestinal villus of small intestine for broiler chickens in the control group were necrotic and dissolved, incomplete in structure, and accompanied by massive bleeding. After the treatment with tectorigenin, the histopathological injury described above was significantly alleviated. The result of daily weight gain showed that the daily weight gain of broiler chickens in the treatment group was similar to that of broiler chickens in the healthy group, both of which were significantly higher than that of the infected group.

The above results indicated that tectorigenin has a good protective effect on chicken necrotic enteritis caused by *Clostridium perfringens*.

The positive effect of the present disclosure is to provide a new medical use of tectorigenin for the treatment of chicken necrotic enteritis, which can significantly reduce the degree of pathological changes in the intestinal tract of chickens with necrotic enteritis, and has a good therapeutic effect on chicken necrotic enteritis caused by *Clostridium perfringens*.

BRIEF DESCRIPTION OF DRAWINGS

FIG. 1 is an image showing that tectorigenin can significantly inhibit the gliding motility of *Clostridium perfringens* on BHIA;

FIG. 2 is an image showing that tectorigenin can effectively inhibit the biofilm formation of *Clostridium perfringens;*

FIG. 3 is an image showing the scoring of intestinal injury performed according to the degree of intestinal injury;

FIG. 4 is a picture showing the histopathological changes observed under a microscope;

FIG. 5 is an image showing the effect of tectorigenin treatment on the daily weight gain of broiler chickens with necrotic enteritis.

DETAILED DESCRIPTION

Example 1

Provided is use of tectorigenin in the preparation of a medicament for the treatment of chicken necrotic enteritis, and any pharmaceutically dosage form prepared from tectorigenin as an active ingredient.

Example 2

The chicken necrotic enteritis treated with tectorigenin is necrotic enteritis caused by bacteria.

Example 3

The chicken necrotic enteritis treated with tectorigenin is necrotic enteritis caused by *Clostridium perfringens*.

The invention claimed is:

1. A method for treating chicken necrotic enteritis, comprising administering to chicken a therapeutically effective amount of tectorigenin.

2. The method according to claim 1, wherein the chicken necrotic enteritis is necrotic enteritis caused by bacteria.

3. The method according to claim 1, wherein the chicken necrotic enteritis is necrotic enteritis caused by *Clostridium perfringens*.

* * * * *